| United States Patent [19] | [11] 4,122,086 |
|---|---|
| Hall et al. | [45] Oct. 24, 1978 |

[54] ISOPENICILLINS

[75] Inventors: Ralph Floyd Hall, Cranbury, N.J.; William Francis Huffman, Malvern, Pa.

[73] Assignee: SmithKline Corporation, Philadelphia, Pa.

[21] Appl. No.: 819,197

[22] Filed: Jul. 26, 1977

[51] Int. Cl.$^2$ .......................................... C07D 513/04
[52] U.S. Cl. ............................. 260/306.7 R; 424/270
[58] Field of Search ................................. 260/306.7 R Primary Examiner—Jose Tovar
Attorney, Agent, or Firm—Stuart R. Suter; Alan D. Lourie; William H. Edgerton

[57] ABSTRACT

A new bicyclic β-lactam containing the novel 7-oxo-1-aza-3-thiabicyclo[3.2.0]heptane nucleus (isopenicillin) is disclosed. The compounds have antibacterial activity against gram positive and gram negative organisms. Intermediates useful for the preparation of these active products are also disclosed.

15 Claims, No Drawings

ISOPENICILLINS

BACKGROUND

Since the 1940's penicillins have played an important role in the chemotherapy of infectious disease. Much research has been done and many derivatives of penicillins have been prepared. A number of penicillins have shown sufficient antibacterial activity to be commercialized. This large amount of research in all commercial products have been directed to penicillins which contain the 7-oxo-1-aza-4-thiabicyclo[3.2.0]heptane nucleus. Work on the total synthesis of penicillins has also been studied by various investigators but this work also has been directed to preparing compounds with the same 1-aza-4-thiabicycloheptane nucleus.

A small amount of research has been conducted in an attempt to prepare penicillins with an unnatural nucleus. Examples of these include systems without the α-methyl groups or in which the sulfur atom is at a different position in the ring system. One unsuccessful attempt at preparing the 7-oxo-3-thia-1-azabicyclo[3.2.0]heptane-2-carboxylic acid system has been reported in the literature; J. Chem. Soc.(C), 188 (1971). The trivial name for this bicyclic nucleus has been recently proposed as isopenicillin, Can. J. Chem., 55, 468 (1977).

We now wish to report the successful synthesis of compounds containing the isopenicillin nucleus. These compounds are prepared by a total synthetic method, and have antibacterial activity.

DESCRIPTION OF THE INVENTION

The compounds of this invention are represented by the following structural formula:

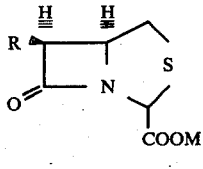

Formula I wherein
R is acylamino, azido or amino and
M is hydrogen, a pharmaceutically acceptable cation, or a carboxylic acid protecting ester residue.

Within the term acylamino, acyl refers to acyl groups represented by the general formulae:

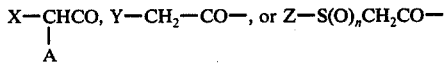

where
X is thienyl, furyl, cyclohexyl, cyclohexenyl, cyclohexadienyl, phenyl or phenyl substituted with one or two substituents selected from the group consisting of lower alkyl, lower alkoxyl, hydroxy, hydroxymethyl, halo, nitro, mercapto, lower alkylthio, trifluoromethyl, ureido, formamido, and carboxymethylamino;
A is hydroxy, formyloxy, carboxyl, sulfo or (when the α-hydrogen is absent) methoxyimino or oximino;
Y is cyano, azido, phenyl, phenoxy or a 5 or 6-membered heterocyclic ring containing carbon and 1–4 heteroatoms selected from the group consisting of nitrogen, oxygen and sulfur;
Z is phenyl, pyridyl, lower alkyl, trifluoromethyl, trifluoroethyl, or cyanomethyl; and
n is 0, 1 or 2.

The 5- or 6-membered heterocyclic rings referred to above include thienyl, furyl, thiazoyl, isothiazolyl, oxadiazolyl, thiadiazolyl, triazolyl, tetrazolyl, pyridyl, pyrimidyl and the like. Each heterocyclic group may be unsubstituted or substituted with one or two substituents selected from lower alkyl, halo, hydroxy, nitro, lower alkoxy, aryl such as phenyl, lower aralkyl and the like. The terms lower alkyl or lower alkoxy refer to groups containing one to six carbon atoms.

Particularly preferred acyl groups include the following examples:

phenylacetyl
α-hydroxyphenylacetyl
α-formyloxyphenylacetyl
trifluoromethylmercaptoacetyl
methylmercaptoacetyl
methylsulfonylacetyl
2,2,2-trifluoroethylsulfinylacetyl
cyanoacetyl
cyanomethylmercaptoacetyl
60 -carboxy-2-thienylacetyl
α-carboxy-3-thienylacetyl
α-carboxyphenylacetyl
α-sulphophenylacetyl
2-thienylacetyl
1-tetrazolylacetyl
phenoxyacetyl
4-pyridylmercaptoacetyl
syn-α-methoxyimino(2-furyl)acetyl
α-oximinophenylacetyl
2,6-dimethoxybenzoyl The isopenicillin compounds of this invention decompose rapidly when the 2-carboxylic acid group is present in the free acid form. However, the compounds are stable when the acid is present as a salt or is protected with a protective ester. Therefore, it is apparent to the skilled chemist that all chemical reactions performed on these compounds must be done under conditions which take this fact into account.

The term "a carboxylic acid protective ester residue" refers to those ester groups which are commonly employed to block or protect the carboxylic acid functionality while reactions are carried out on other functional groups within the molecule. The term has acquired a definite meaning within the β-lactam and organic chemical arts and many useful groups within this term are known in the art. These protective groups are known for the ease with which they may be cleaved to regenerate the carboxylic acid group. As used within this disclosure, the term refers to those groups known in the art which can be cleaved by mild basic hydrolysis and/or hydrogenation in basic solution.

Known ester protecting groups include lower alkyl such as methyl, 2,2,2-trichloroethyl, β-iodoethyl, $C_1$-$C_6$-alkanoylmethyl, N-phthalimidomethyl, benzoylmethyl, halobenzoylmethyl, methylbenzoylmethyl, methanesulfonylbenzoylmethyl, phenylbenzoylmethyl, benzyl, p-nitrobenzyl, p-methoxybenzyl, benzhydryl and the like. The choice of which ester group to use is well within the ability of one skilled in the art. Factors which are considered include what subsequent reaction conditions the group must withstand and what conditions for removing the protecting ester is desirable. Particularly preferred esters are methyl, benzyl and benzhydryl. The selection of the proper protecting group is not critical to our invention since the point of novelty of our invention lies within the new isopenicillin nucleus and not within the ester groups substituted thereon.

The above definition of carboxyl protecting groups is not intended to be exhaustive. A person skilled in the art knows the purpose of these groups and is able to properly choose from the groups known and described in the art. Many articles and books have described the subject of protecting reactive groups, for example J. F. W. McOmie, "Protective Groups in Organic Chemistry", Plenum Press, 1973.

to sterilize laboratory equipment or for the treatment or prevention of bacterial infections in warm-blooded mammals such as man.

The compounds where R is acylamino and M is a carboxylic acid protecting ester group also exhibit antibacterial activity, for example against *B. subtilis*. These compounds may be used in the same manner as described for the compounds where M is not an ester.

The compounds of this invention where R is amino or azido and/or M is a carboxylic acid protecting ester group are useful as intermediates for the preparation of the therapeutically active compounds. When R is azido, reduction by chemical or catalytic methods also gives the useful free amino derivative.

Within this disclosure the terms halogen or halo shall mean fluorine, chlorine, bromine or iodine.

Table 1

| | MINIMUM INHIBITORY CONCENTRATION (μg/ml) | | | | | | | |
|---|---|---|---|---|---|---|---|---|
| | 1 | 2 | 3 | 4 | 5 | 6 | 7 | 8 |
| Compound (R in Formula I) | Staph. aureus HH 127 | Staph. aureus SK&F 23390 | Staph. aureus Villaiuz (M.R.) SK&F 70399 | Strep. faecalis HH 34358 | E. coli SK&F 12140 | E. coli HH 33779 | Kleb. pneumoniae SK&F 4200 | Kleb. pneumoniae SK&F 1200 |
| Ph-OCH$_2$CONH* | >400 | 12.5 | >400 | >400 | >400 | >400 | >400 | >400 |
| Thienylacetamido | >400 | 6.3 | >400 | 50 | 25 | 25 | 12.5 | 25 |
| Penicillin VK | 200 | ≥0.1 | 200 | 1.6 | 100 | 200 | 50 | 200 |
| Thienylmethyl-penicillin | 50 | 0.1 | 200 | 0.8 | 12.5 | 25 | 3.1 | 25 |
| | 9 | 10 | 11 | 12 | 13 | 14 | 15 | |
| Compound (R in Formula I) | Salmonella paratyphi ATCC 12176 | P. mirabilis PH-444 | Pseudo. aeruginosa HH 63 | Serratia marcescens ATCC 13880 | Proteus morgani 179 | Enterobacter aerogenes ATCC 13048 | Enterobacter cloacae HH 31254 | |
| Ph-OCH$_2$CONH* | 400 | 400 | >400 | >400 | >400 | >400 | >400 | |
| Thienylacetamido | 3.1 | 12.5 | 400 | 200 | 400 | 25 | 25 | |
| Penicillin VK | 100 | — | >200 | >200 | >200 | 200 | 50 | |
| Thienylmethyl-penicillin | 1.6 | 1.6 | 100 | 100 | >200 | 25 | 6.3 | |

*Compound assayed for 30% β-lactam by hydroxylamine assay.

The term "pharmaceutically acceptable cation" is also a well known term in the art. Many bases are known and used to prepare salts of carboxylic acids for pharmaceutical formulations. These salts have improved properties, such as solubility, over the free acids. Examples of useful cations include alkali metals such as sodium and potassium, alkali earth metals and ammonium cations from inorganic or organic amine bases. These salts are prepared when the protective ester groups are hydrolyzed by base or when the isopenicillin nucleus is formed by base treatment as described below.

Also included within the scope of this invention is the salts of other acid moieties present within the acyl group of the compounds. These salts are prepared in the same manner as described above.

The compounds of this invention may exist in hydrate or solvate form. The amount of water or solvent may vary. These various forms of the compounds of this invention are also part of the invention disclosed and claimed herein.

The compounds of this invention where R is acylamino and M is hydrogen or a pharmaceutically acceptable cation have antibacterial activity against Gram-positive and Gram-negative organisms. Minimum inhibitory concentrations (MIC's) against a variety of bacteria is shown in Table 1 for representative compounds. Data for standard antibacterial agents, penicillin V and 2-thienylmethylpenicillin are included. The active compounds or their salts can be dissolved in water and used The compounds of this invention are novel bicyclic β-lactams which are prepared by a totally synthetic route. The key starting materials are cis-3-azido-4-oxo-2-azetidinylmethyl iodide (1a) and cis-3-t-butoxycarbonylamino-2-hydroxymethyl-4-oxoazetidine (1b). These compounds are prepared in good yield

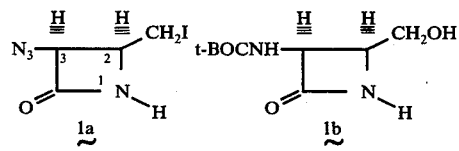

via a ketene-imine cyclization reaction of azidoacetic acid and methyl N-(2,4-dimethoxybenzyl)iminoacetate and subsequent chemical modification, all as set forth in Belgian Pat. No. 841,234.

The conversion of compound 1a or 1b into the compounds of this invention involve modifications of the various substituents by a series of chemical reactions. Schemes 1, 2 and 3 set forth different reactions which may be used to prepare compounds of this invention. It is readily apparent to one skilled in the art that the reactions set forth in these Schemes may be carried out by various methods in various sequences. In particular, at various points along the reaction pathway set forth in each of the Schemes, the R substituent may be converted from azido to amino and the amino group subsequently acylated with a desired acyl group. The most advantageous times to perform these conversions would be readily apparent to a person skilled in the art.

The reaction sequence set forth in Scheme 1 involves first, a condensation of the β-lactam 1 with an ester of glyoxylic acid to give the α-hydroxy-α-azetidinylacetic acid derivative (2). The hydroxy group of this compound is converted to a halo derivative, such as chloro by the reaction with thionyl chloride, and the halo derivative is reacted with a salt of thiolacetic acid to give the sulfur-containing compound (3). Cyclization of compound (3) to the desired isopenicillin derivative can be effected by treatment with a base such as cyclohexylamine. If R is azido, reduction to the amino derivative followed by acylation with the desired acyl group gives the compounds of this invention. If M is a protecting ester group, it may be removed by base hydrolysis to give the compounds where M is a cation.

SCHEME 1

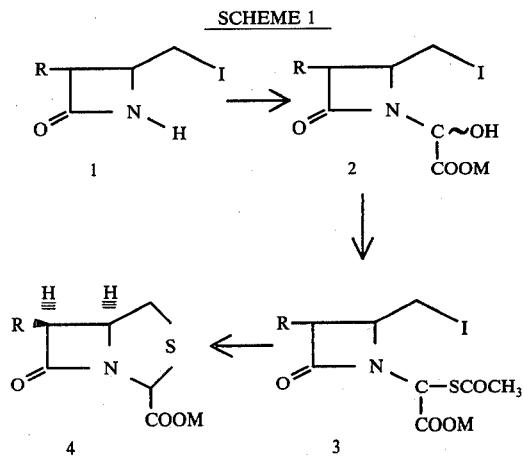

Within Scheme 1 a preferred route to the antibacterial compounds of this invention involves treating compound 3 where R is acylamino and M is a cation such as sodium with a base such as cyclohexylamine. Starting with compound 1 where R is t-butoxycarbonylamino (which is prepared by reacting compound 1b with tosyl chloride followed by sodium iodide), condensation with benzhydryl glyoxylate gives compound 2 (R is t-butoxycarbonylamino and M is benzhydryl). Treatment with thionyl chloride followed by potassium thiolacetate gives compound 3 (R and M are as above). Treatment with a strong acid such as trifluoroacetic acid hydrolyzes both the t-butoxycarbonyl and benzhydryl groups to give the salt of compound 3 where R is amino. Acylation of this amino compound by standard methods gives the compounds where R is acylamino. Any protecting groups within the acyl moiety are removed and the compound is converted to the acid salt which is treated with base as described above to give the desired products.

Within the preferred route set out above, various bases may be used. In particular, any organic primary and secondary amine which preferentially hydrolyzes the thiolacetate moiety over attacking the β-lactam moiety gives the desired product. The selectivity of action is a result of choosing a base with the proper balance between basicity and nucleophilicity. The selection of the proper base is within the ability of a person skilled in the art.

The preferred route is run in an organic solvent, preferably an aprotic solvent. The reaction is run at a temperature and a period of time which maximizes the formation of product and minimizes product decomposition. Temperatures may range from −30° to 30° with about 0° being a preferred temperature.

Scheme 2 sets forth a different reaction sequence for converting the α-hydroxy compound 2 into the isopenicillins. The hydroxy group is converted into a chloro group as outlined above in Scheme 1. The resulting chloro derivative is treated with sodium triphenylmethylmercaptide to give derivative 4. Cyclization of derivative 4 can be effected by treatment with metal ions such as silver or mercury or by treatment with a strong acid such as trifluoroacetic acid.

SCHEME 2

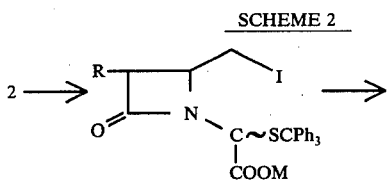

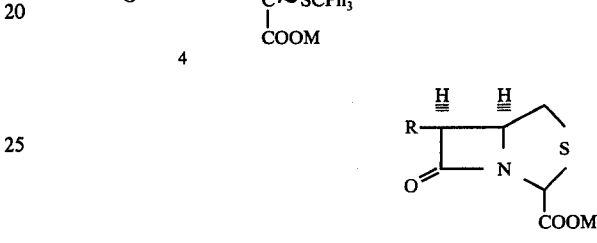

The α-chloro compound (5) may also be converted directly into the desired isopenicillin as outlined in Scheme 3. Reagents useful for this conversion include hydrogen sulfide, sodium hydrosulfide, sodium sulfide and tetramethylguanidinium hydrosulfide.

SCHEME 3

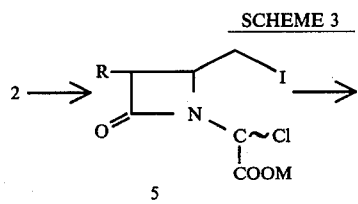

Acylations of the compounds of this invention are effected by standard methods. The carboxylic acid group which will be the carbonyl group in the acyl moiety is activated by known methods including mixed anhydride, activated esters, and acid halides. In addition, use of coupling reagents such as dicyclohexylcarbodiimide and carbonyldiimidazole is a possible method of acylation. During the acylation reaction, any sensitive group in the acyl moiety, for example, hydroxyl or carboxyl, can be protected by a standard protecting group such as those described previously and/or known in the art. At the appropriate time, which was suggested in the above discussion of preparation of these compounds or at such other time which would be apparent to one skilled in the art the protecting group can be removed.

Various acyl groups which are particularly useful in this invention contain an assymetric carbon atom. It is understood that each optical isomer separately and as mixtures of the isomers are within the scope of this invention. It has been found that the D-isomer is particularly useful and therefore is a preferred isomer as with the mandelamido containing compounds.

In addition, the cis-fused isopenicillin ring system may exist as $d$ and $l$ isomers. The carboxylic acid group at position 2 can be in the $\alpha$ or $\beta$ configuration and results in an additional center of asymmetry. All possible stereoisomers are within the scope of this invention.

The starting materials necessary to prepare the compounds of this invention are commercially available, described herein or prepared by methods known in the art and readily apparent to a person skilled in the art.

The following examples are presented to illustrate general methods of preparing the compounds of this invention to one skilled in the art and are not to be construed as limitative of the scope thereof. All temperatures are given in degrees Centigrade.

PREPARATION 1 cis-3-Azido-4-oxo-2-azetidinylmethyl iodide

A degassed solution of cis-3-azido-4-oxo-2-azetidinylmethyl tosylate (2.36 g) in acetone (80 ml) was refluxed with NaI (5.85 g) overnight. Reaction was cooled and the acetone was removed in vacuo. The reaction mixture was partitioned between ethyl acetate and aqueous sodium thiosulfate solution. Phases were separated and the organic layer was extracted with thiosulfate solution. The combined aqueous extracts were extracted with ethyl acetate. The combined ethyl acetate layers were washed with brine, dried and evaporated to give an off-white solid. The product was recrystallized from ethyl acetate-hexane, melting point 130°–2° (dec.), 1.5 g (75%).

PREPARATION 2 cis-3-Azido-4-oxo-2-azetidinylmethyl bromide

A degassed solution of cis-3-azido-4-oxo-2-azetidinylmethyl tosylate (0.41 g, 1.4 mmol) in dimethylformamide (5 ml) was heated to 90° with LiBr (0.43 g, 5 mmol) for 4 hours. The reaction was poured into ethyl acetate and washed copiously with water. The dried solution was evaporated to give the title compound.

PREPARATION 3

Benzyl α-(cis-3-azido-2-iodomethyl-4-oxoazetidinyl)-α-hydroxyacetate

Benzyl glyoxylate (1.97 g, 12 mmol) was dissolved in toluene (25 ml) and a small amount was distilled out to dry the solution. The solution was cooled to 90° and the product of Preparation 1 (1 g, 3.97 mmol) was added. The reaction was heated for 5.5 hours under argon at 90°. The solution was evaporated in vacuo and the residue was chromatographed on silica gel (100 g). The product was eluted with 10% ethyl acetate in benzene, 1.28 g (78%).

PREPARATION 4

Benzyl α-(cis-3-azido-2-iodomethyl-4-oxoazetidinyl)-α-chloroacetate

A solution of compound from Preparation 3 (130 mg, 0.31 mmoles) in methylene chloride (3 ml) was stirred under an argon atmosphere at −10° and treated with pyridine (28.2 μl, 0.35 mmol) and thionyl chloride (24.9 μl, 0.35 mmol). The reaction was stirred for 20 minutes and the solvents were removed in vacuo. The residue was partitioned between ethyl acetate and water. The organic phase was separated, washed with water and brine, dried and evaporated. The residue was chromatographed on silica gel (10 g) and the product was eluted with 2% ethyl acetate in benzene to give the title product, 102 mg (72%).

PREPARATION 5

Benzhydryl α-(cis-3-azido-2-iodomethyl-4-oxoazetidinyl)-α-hydroxyacetate

A solution of benzhydryl glyoxylate (3.9 g, 16 mmol) in toluene (40 ml) was heated to reflux under an argon atmosphere and 2 ml of toluene was removed by distillation. The toluene solution was allowed to cool to ca. 80° C. and the 3-azido-4-oxo-2-azetidinemethyl iodide (1.5 g, 5.95 mmole) was added. The reaction mixture was heated at 85°–90° C. for 5 hrs. and then was cooled and the solvents were removed in vacuo. Chromatography of the residue on silica gel using ethyl acetate-dichloromethane as eluant afforded the product as a clear colorless gum. Upon standing at room temperature for several hours, one diastereoisomer crystallized and was isolated and recrystallized from ether-hexane to give a white solid, m.p. 125°–127° (dec.).

PREPARATION 6

Benzyl α-(cis-3-azido-2-iodomethyl-4-oxyazetidinyl)-α-thioacetoxyacetate

A solution of the compound of Preparation 3 (520 mg, 1.25 mmol) in tetrahydrofuran (10 ml) was cooled to −10° under argon and treated with pyridine (113 μl, 1.4 mmol) followed by thionyl chloride (100 μl, 1.4 mmol). After stirring 20 minutes, a suspension of sodium thiolacetate (137 mg, 1.5 mmol) in dimethylformamide (8 ml) was added. The reaction was stirred for 45 minutes at −10° and then for 2 hours at room temperature. The solvents were removed and the residue dissolved in ethyl acetate. The organic solution was washed with water and brine, dried, and evaporated. The residue was chromatographed on silica gel (75 g) and the title product was eluted with 3% ethyl acetate in benzene, 400 mg (67%).

PREPARATION 7

Benzhydryl α-(cis-3-azido-2-iodomethyl-4-oxoazetidinyl)-α-thioacetoxyacetate To a stirred solution of product from Preparation 5 (0.514 g, 1.19 mmole) in anhydrous tetrahydrofuran (17 ml) at −20° under argon was added anhydrous pyridine (99 μl, 1.21 mmol) followed by thionyl chloride (87 μl, 1.21 mmol). The reaction mixture was stirred at −20° for 0.5 hr. A solution of potassium thiolacetate (0.209 g, 1.8 mmole) in anhydrous N,N-dimethylformamide (16 ml) was added. The reaction was allowed to come to ambient temperature over a period of 1 hr. and then was poured into ethyl acetate and extracted five times with water. The combined aqueous extracts were extracted once with ethyl acetate and the combined ethyl acetate extracts were dried. Evaporation of the solvents in vacuo afforded a yellow gum which was purified by silica gel chromatography. Elution with ethyl acetate-dichloromethane gave the desired product as a semi-crystalline, light-yellow gum. Recrystallization from ethyl acetate-hexane afforded a white solid, m.p. 133°–135° (dec) which was a single diastereoisomer.

PREPARATION 8 cis-3-t-Butoxycarbonylamino-4-oxo-2-azetidinylmethyl bromide

A solution of cis-3-t-butoxycarbonylamino-2-hydroxymethyl-4-oxoazetidine (36 g, 0.166 mol) in pyridine (200 ml) was cooled in an ice-salt bath to −7° and treated with methanesulfonyl chloride (20.2 ml, 29.9 g, 0.261 mol) dropwise over a period of 23 minutes. When the addition was completed the reaction was stirred with continued cooling for 2.5 hours and then poured into ice water (700 ml). The precipitated solid was collected, washed with water and dried; 36.1 g, mp 151° (dec). Concentration of the mother liquors yielded a second crop of product; 3.6 g, mp 148.5°–149° (dec).

To a mixture of LiBr (49.0 g, 0.565 mol), $Na_2CO_3$ (22 g) an dry dimethylformamide (450 ml) was added under a nitrogen atmosphere the above mesylate (33.3 g, 0.113 mol). The reaction was heated at 80° for 4.5 hours. The solution was filtered and the filtrate was concentrated in vacuo. The residue was triturated with ice water and the resulting solid was collected, washed generously with water and dried to give the title compound as a white solid; 24.1 g (76%).

PREPARATION 9

Benzhydryl α-(cis-3-t-butoxycarbonylamino-2-bromomethyl-4-oxoazetidinyl)-α-hydroxyacetate A solution of benzhydryl glyoxalate monohydrate (56.8 g, 0.22 mol) in dry dioxane (550 ml) was stirred over 40 grams of molecular sieves (4A) for 0.5 hours and then the product from Preparation 8 (55.8 g, 0.2 mol) was added followed by additional dry dioxane (50 ml) and dry triethylamine (27.6 ml, 0.2 mol). The reaction was stirred at room temperature for 3 hours and then filtered. The filtrate was evaporated in vacuo and the residue dissolved in ethyl acetate (300 ml). The solution was washed with dilute HCl (100 ml), 5% $NaHCO_3$ (100 ml), water (100 ml), saturated $NaHCO_3$ (2 × 100 ml) and water (100 ml). The dried organic layer was evaporated and the residue was dissolved in ether (300 ml). Upon cooling, the product crystallized and was collected; 81.8 g, mp 133°–137°.

PREPARATION 10

α-(cis-3-amino-2-bromomethyl-4-oxoazetidinyl)-α-thioacetoxy-acetic acid

A solution of the product from Preparation 9 (8.5 g, 0.016 mol) in dry tetrahydrofuran (140 ml) was dried over molecular sieves (4A) under nitrogen for 30 minutes at 0°. To this solution was added dry pyridine (3.2 g, 0.04 mol) followed by the dropwise addition of distilled thionyl chloride (3.8 g, 0.032 mol). After stirring at 0° for 45 minutes, the solution was cooled to −15° and treated dropwise with a solution of potassium thiolacetate (5.5 g, 0.048 mol) and dry dimethylformamide (140 ml) which had been dried over molecular sieves (4A) for 1 hour. The reaction was stirred at −15° for 1 hour and then at 0° for 2 hours. The solvents were removed in vacuo and the residue dissolved in ethyl acetate. The organic solution was washed with dilute HCl, 5% $NaHCO_3$, water and saturated brine. The dried organic phase was concentrated in vacuo and the residue was dissolved in ether. The dropwise addition of petroleum ether and cooling resulted in the formation of a white solid product which was collected and washed with ether; 6.35 g (69%).

For 20 minutes gaseous HCl was passed through a $H_2SO_4$ trap and then was bubbled into dry nitromethane (10 ml) which was cooled in an ice bath. To this solution was added the above product (0.57 g, 1 mmol) and the reaction was stirred for 30 minutes during which time a white precipitate formed. Ether was added and the resulting solid was collected, washed with ether and dried to give the title product as its hydrochloride salt; 0.3 g (86%).

PREPARATION 11

[cis-3-(2-Thienylacetamido)-2-bromomethyl-4-oxoazetidinyl]-thioacetoxyacetic acid To a cold (0° C.) solution of the product of Preparation 10 (0.35 g, 1 mmol) in dry chloroform (25 ml) was added diisopropylethylamine (0.43 g, 33 mmol) followed by a dropwise addition of freshly distilled thienylacetic acid chloride (0.176 g, 11 mmol). Reaction solution was stirred at 0° C. for 3 hours and then was extracted with 3N HCl followed by 5% $NaHCO_3$. The basic aqueous extract was acidified to pH 1.5 with dilute HCl and extracted several times with ethyl acetate. The organic phases were combined, dried, concentrated to one-third of the volume which was added to stirring petroleum ether and the precipiated product was collected (300 mg). An analytical sample was obtained by trituration with ether.

PREPARATION 12

Benzyl α-(cis-3-phenoxyacetamido-2-iodomethyl-4-oxoazetidinyl)-α-(triphenylmethylthio)acetate To a stirred solution of compound from Preparation 13 (3.71 g, 7.08 mmol) in tetrahydrofuran (50 ml) at −15° under an argon atmosphere was added pyridine (0.642 ml, 7.95 mmol) and thionyl chloride (0.568 ml, 7.95 mmol). The reaction was stirred for 15 minutes and then a suspension of sodium triphenylmethylmercaptide (17.5 mmol) in tetrahydrofuran (24 ml) was added. The mixture was stirred for 15 minutes at −18° and then allowed to warm to room temperature over a 1 hour period. The solvent was removed and the residue partitioned between water and ethyl acetate. The aqueous phase was extracted with ethyl acetate and the combined organic phases were washed with brine, dried, and evaporated. The resulting residue was chromatographed on silica gel (300 g) to give 2.5 g of crude title product. Recrystallization from ethyl acetate-hexane gave a white crystalline product, 2.01 g (36%), mp 155°–7° (dec.).

PREPARATION 13

Benzyl (cis-3-Phenoxyacetamido-2-iodomethyl-4-oxoazetidinyl)-α-hydroxyacetic acid To a suspension of cis-3-phenoxyacetamido-4-oxo-2-azetidinemethyl iodide (5.00 g, 0.014 mol) and freshly distilled benzyl glyoxylate (11.4 g, 0.0695 mol) in anhydrous tetrahydrofuran (100 ml) at 23° C. under an atmosphere of argon was added freshly distilled boron trifluoride etherate (3.42 ml, 0.0278 mol). After 45 minutes at 23° C. the reaction mixture was poured into a solution of sodium bicarbonate (2.5 g) in water (25 ml). The reaction was extracted with ethyl acetate and the product isolated in the usual way to give crude material (16 g) which was dissolved in dichloromethane and allowed to crystallize overnight at −23° C. The solution was filtered and the crystals dried to give a white crystalline solid; 2.6 g, mp 159°–160.5°. The mother liquors were combined and chromatographed on silica gel to afford additional semi-crystalline product (3.71 g). The crystalline material was a single diastereoisomer while the material isolated by chromatography was a mixture of diastereoisomers.

PREPARATION 14

Sodium α-[cis-3-(2′-Thienylacetamido)-2-iodomethyl-4-oxo-1-azetidinyl]-α-thioacetoxyacetate To a suspension of 1.78 g (5.08 mmol) of cis-3-(2′-thienylacetamido)-4-oxo-2-azetidinylmethyl iodide (Belgian Pat. No. 841,234) and 2.66 g (16.2 mmol) of freshly distilled benzyl glyoxylate in 44 ml of anhydrous tetrahydrofuran under an argon atmosphere is added 1.31 ml (10.6 mmol) of freshly distilled boron trifluoride etherate. The reaction mixture is stirred at ambient temperature for 1.25 hours, poured into aqueous $NaHCO_3$ and extracted with ethyl acetate. The combined extracts are washed copiously with water and brine. The dried extracts are distilled in vacuo to give 4.5 g of clear orange gum which was rapidly chromatographed on a column of 90 g of silica gel with methylene chloride and 20% ethyl acetate in methylene chloride as eluants to give the condensation product, 1.66 g (64%).

The above product is reacted with pyridine and thionyl chloride at −20° for 45 minutes and then with potassium thiolacetate, all according to the procedure given in Preparation 10 to give the thioacetoxy product. Recrystallization from ethyl acetatehexane gave the benzyl ester of the thioacetoxy derivative as a white crystalline solid, mp 159°–62°.

A solution of 1.05 g (7.6 mmol) of anhydrous potassium carbonate in 50 ml of water is deoxygenated and cooled to 0° under argon. To this mixture is added a solution of 0.796 g (1.39 mmol) of above benzyl ester in 36 ml of tetrahydrofuran. The reaction is deoxygenated again and stirred at 0° for ca. 5 min and then without cooling for a total of 1 hour. The mixture is poured into 200 ml of ethyl acetate and extracted with 5% aq. $NaHCO_3$, water and brine. The aqueous extracts are combined, acidified to pH 2 with conc. $H_3PO_4$, and then saturated with NaCl. The aqueous solution is extracted with ethyl acetate. The dried extracts are evaporated to give 0.493 g (73%) of crude acid which is chromatographed on silica gel with an eluant of 70:23:5:2 ethyl acetate:acetone:methanol:water. The acid is converted to its sodium salt by treating 0.525 g of the acid with 80 mg $NaHCO_3$ in water and then lyophilizing the solution to obtain the sodium salt.

EXAMPLE 1

Benzyl 6β-azido-7-oxo-3-thia-1-azabicyclo[3.2.0]heptane-2-carboxylate

Method A

To a stirred solution of the product from Preparation 6 (88 mg, 0.186 mmol) dissolved in dichloromethane (3 ml) at 0° under argon was added cyclohexylamine (52 μl, 0.45 mmol). The reaction was stirred at 0° for 90 minutes and then at room temperature for 30 minutes. The reaction solution was partitioned between ethyl acetate and 1N sulfuric acid. The organic phase was separated and washed with pH 7 buffer and brine. The dried solution was evaporated to give a crude product which was chromatographed on silica gel (10 g) with 2% ethyl acetate in benzene as eluant to give the title product, 37 mg (66%), mp 68°–69°.

Method B

A solution of the compound from Preparation 4 (98 mg, 0.226 mmol) and pyridine (100 μl, 1.24 mmol) in tetrahydrofuran (5 ml) under an argon atmosphere at 0° was treated with hydrogen sulfide for 20 minutes. The reaction mixture was stirred for 90 minutes at 0° and then purged with nitrogen. The solvent was removed and the residue was partitioned between ethyl acetate and water. The organic phase was separated, washed with water and brine, dried, and evaporated. The residue was chromatographed on silica gel (10 g) with 2% ethyl acetate in benzene as eluant to give the title product, 21 mg (33%).

EXAMPLE 2

Benzhydryl 6β-azido-7-oxo-3-thia-1-azabicyclo[3.2.0]heptane-2-carboxylate

A cold solution (0°) of thiolacetate from Preparation 7 (32 mg, 0.058 mmol) and anhydrous dichloromethane (1 ml) under an argon atmosphere was treated with cyclohexylamine (16 μl, 0.132 mmol). The reaction was stirred at 0° for 1 hour and then at 22° for 2 hours. The mixture was poured into ethyl acetate and extracted with dilute aqueous sulfuric acid and then with brine. The ethyl acetate phase was dried and evaporated to give a semi-crystalline residue. The product was chromatographed on silica gel with 1% ethyl acetate in benzene as eluant to give the pure title compound, 20 mg (91%).

EXAMPLE 3

Benzhydryl 6β-amino-7-oxo-3-thia-1-azabicyclo[3.2.0]heptane-2-carboxylate

The compound from Example 2 (65 mg, 0.171 mmol) was hydrogenated at atmospheric pressure in ethyl acetate (2 ml) in the presence of $PtO_2$ (130 mg) for 3 hours. The mixture was filtered and evaporated to give the title product, 60 mg.

EXAMPLE 4

Benzyl 6β-amino-7-oxo-3-thia-1-azabicyclo[3.2.0]heptane-2-carboxylate

The compound of Example 1 (35 mg, 0.115 mmol) was hydrogenated in ethyl acetate with $PtO_2$ as catalyst (70 mg) in the same manner as in Example 3 to give the title product, 32 mg.

EXAMPLE 5

Benzyl 6β-phenylacetamido-7-oxo-3-thia-1-azabicyclo[3.2.0]-heptane-2-carboxylate To a cold solution (0°) of the 6-amino derivative of Example 4 (56 mg, 0.2 mmol) in methylene chloride (2 ml) under argon was added triethylamine (27.7 μl, 0.2 mmol) and then phenylacetyl chloride (26.4 μl, 0.2 mmol). The reaction was stirred for 30 minutes and then the solvents were evaporated. The residue was chromatographed on silica gel (5 g) with 30% ethyl acetate in cyclohexane as eluant to give the title product, 26.1 mg (33%).

EXAMPLE 6

Benzyl 6β-phenoxyacetamido-7-oxo-3-thia-1-azabicyclo[3.2.0]-heptane-2-carboxylate Substitution of phenoxyacetyl chloride for phenylacetyl chloride in Example 5 gives the title compound. The product was purified by chromatography on silica gel with 10% ethyl acetate in benzene as eluant, 11 mg (24%).

EXAMPLE 7

Benzhydryl 6β-(2'-thienylacetamido)-7-oxo-3-thia-1-azabicyclo[3.2.0]heptane-2-carboxylate The 6-amino benzhydryl ester of Example 3 (60 mg, 0.17 mmol) was acylated in dichloromethane with 2'-thienylacetyl chloride (14.2 μl, 0.12 mmol) in the presence of triethylamine (16.5 μl, 0.12 mmol) all according to the procedure of Example 5. Crude product was chromatographed on silica gel and eluted with 10% ethyl acetate-benzene to give the title product, 20.3 mg (36%).

EXAMPLE 8

6β-Phenoxyacetamido-7-oxo-3-thia-1-azabicyclo[3.2.0]heptane-2-carboxylic acid sodium salt A solution of benzyl ester in Example 6 (102 mg, 0.248 mmol) in 50% aqueous tetrahydrofuran (1 ml) was cooled to 0° under argon and treated dropwise with 0.1N NaOH (1 ml). Additional NaOH was added after 5 minutes (1 ml) and after 10 minutes (0.48 ml). The reaction was stirred for 30 minutes at 0° and then was washed with ether (3 × 1 ml). Unreacted starting material was removed by extraction with ethyl acetate. The resulting aqueous solution was lyophilized to give the title product, 27.2 mg (32%).

EXAMPLE 9

6β-(2'-thienylacetamido)-7-oxo-3-thia-1-azabicyclo[3.2.0]-heptane-2-carboxylic acid A solution of the bromothioacetate derivative of Preparation 11 (100 mg, 0.22 mmol) and dichloromethane (20 ml) was treated with cyclohexylamine (0.5 ml, 4.36 mmol) at 0° for 2.5 hours under argon. The solvent was evaporated and hexane was added to the residue. The resulting precipitate was triturated with hexane and ether to give 96 mg of product which contained some starting material. The crude product was suspended in dichloromethane (20 ml) and stirred at 0° under argon with cyclohexylamine (0.5 ml) for 5 hours. The solution was worked up again as described above to give the cyclohexylamine salt of the title compound as a white powder, 85 mg. The product assayed for 0.96 mole of NaBr.

In a similar manner the iodothioacetate derivative of Preparation 14 was converted to the title compound by the procedure set forth above.

EXAMPLE 10

Benzyl 6β-phenoxyacetamido-7-oxo-3-thia-1-azabicyclo[3.2.0]-heptane-2-carboxylate To a solution of a compound from the Preparation 13 (0.233 g, 0.445 mmol) in anhydrous tetrahydrofuran (10 ml) at −20° under an argon atmosphere was added anhydrous pyridine (71 μl, 0.88 mmol) and thionyl chloride (63 μl, 0.88 mmol). The reaction was stirred for 20 minutes with continued cooling and the excess reagents were removed in vacuo. The residue was dissolved in anhydrous dichloromethane (8 ml) and treated with a solution of tetramethylguanidinium hydrosulfide (0.396 g, 2.66 mmol) and anhydrous pyridine (35 μl, 0.43 mmol) in anhydrous dichloromethane (25 ml) which had been cooled to −78° under an argon atmosphere. The reaction mixture was allowed to warm to −10° over a period of 1 hour and then was stirred at room temperature for 0.5 hour. The reaction mixture was extracted with water, dilute HCl, dilute NaHCO$_3$, and brine. The dried organic phase was evaporated and the residue chromatographed on silica gel with ethyl acetate-benzene as eluant to give the title compound as a mixture of diastereoisomers.

EXAMPLE 11

Benzyl 6β-phenoxyacetamido-7-oxo-3-thia-1-azabicyclo[3.2.0]-heptane-2-carboxylate

Method A

A solution of the tritylmercapto derivative of Preparation 12 (78.2 mg, 0.1 mmol) and dichloromethane (2 ml) was treated at room temperature under argon with pyridine (16 μl, 0.2 mmol) and a solution of silver fluoroborate (75 mg, 0.4 mmol) in benzene (2 ml). The reaction was stirred for 30 minutes and then hydrogen sulfide was passed over the solution for 10 minutes. After stirring an additional 20 minutes, the mixture was flushed with argon and the solids were removed. The filtrate was evaporated to give a residue which was chromatographed on silica gel with 20% ethyl acetate in benzene as eluant to give the title product (18 mg).

Method B

The compound of Preparation 12 (731 mg, 0.935 mmol) was dissolved in dichloromethane (30 ml) and anisole (4 ml), cooled to 0° under argon and treated with trifluoroacetic acid (36 ml). The mixture was stirred at 0° for 20 minutes and then was added rapidly to a cold mixture of aqueous NaHCO$_3$ layered with ethyl acetate. The layers were separated and the aqueous layer was reextracted with ethyl acetate. The combined organic phases were washed with brine, dried and evaporated to give the product which was chromatographed on silica gel (100 g). Elution with an ethyl acetate-cyclohexane gradient gave the title product, 273 mg. Repeated chromatography on silica gel with 20% ethyl acetate in benzene as eluant gave pure compound, 102 mg (26%).

Method C

A stirred solution of tritylmercapto derivative of Preparation 12 (23 mg, 0.03 mmol), methanol (2 ml) and dichloromethane (2 ml) was treated at room temperature under argon with mercuric acetate (13.4 mg, 0.042 mmol). The reaction was stirred for 30 minutes and then hydrogen sulfide was passed over the solution. A rapid chromatography on silica gel (1 g) with 10% ethyl acetate and benzene as eluant gave 8 mg of a product which tlc analysis showed to be a mixture of 3 components, one of which was the title compound.

EXAMPLE 12

Benzyl 6β-phenoxyacetamido-7-oxo-3-thia-1-azabicyclo[3.2.0]-heptane-2-carboxylate A stirred solution of hydroxy derivative of Preparation 13 (100 mg, 0.19 mmol) and dry tetrahydrofuran (2.0 ml) was cooled to −10° and treated with pyridine (43.2 μl, 0.55 mmol) and thionyl chloride (38.9 μl, 0.55 mmol). The reaction was stirred for 20 minutes and the solvents were evaporated. The residue was added to a mixture of pyridine (43.2 μl, 0.55 mmol), sodium hydrosulfide (11.2 mg, 0.2 mmol) and dimethylformamide (1 ml) which was cooled to −10°. The reaction mixture was warmed to room temperature and the solvents were removed. The residue was dissolved in ethyl acetate and the resulting solution was washed with water and brine and then evaporated. The residue was dissolved in ethyl acetate and hexane was added to precipitate a solid, 36 mg. The filtrate was evaporated and the residue chromatographed on silica gel (0.5 g) with 2% ethyl acetate in dichloromethane as eluant to give the title product, 12.3 mg (16%).

The title compound was also prepared by dissolving the intermediate chloro compound prepared above in anhydrous dimethylformamide (1.5 ml) and cooling to −20°. The cold solution was treated with a sodium sulfide-dimethylformamide solution (0.7 ml) which was prepared as follows:

A mixture of sodium sulfide nonahydrate (0.546 g) and sulfur (0.073 g, 2.28 mmol) and 95% ethanol (6.7 ml) was refluxed for 30 minutes, cooled slightly and dimethyl formamide (6 ml) was added. The mixture was again heated to reflux and 5.5 ml of distillate was removed to give the desired solution.

The reaction was stirred at −23° overnight and then poured into ethyl acetate and extracted with water. The aqueous extracts were washed with ethyl acetate which was combined with the previous ethyl acetate solution. Evaporation of the organic phase in vacuo gave a solid product (56 mg) which was purified by preparative thin layer of chromatography (silica gel, 20 × 20 cm, 0.5 cm, 20% ethyl acetate-benzene) to give solid product, 32 mg (71%). Recrystallization from ethyl acetate-hexane gave an analytical sample, mp 118°–120.5°.

EXAMPLE 13

Benzyl 6β-phenoxyacetamido-7-oxo-3-thia-1-azabicyclo[3.2.0]-heptane-2-carboxylate To a solution of benzyl α-(cis-3-phenoxyacetamido-2-iodomethyl-4-oxoazetidinyl)-α-hydroxyacetate (0.1 g, 0.19 mmol) in anhydrous tetrahydrofuran (4.0 ml) at −0° C. under an argon atmosphere was added anhydrous pyridine (15.4 μl, 0.19 mmol). followed by thionyl chloride (13.7 μl, 0.191 mmol). The reaction was stirred for 40 minutes and then the reagents were removed by distillation at reduced pressure. The residue was dissolved in dimethylformamide (3 ml) and cooled to 0° under argon and treated with a solution of the sodium salt of p-methoxybenzylmercaptan which was prepared by suspending sodium hydride (19 mg, 0.45 mmol, 57% oil dispersion) in anhydrous tetrahydrofuran, adding the mercaptan (55 μl, 0.39 mmol), removing the tetrahydrofuran by distillation once hydrogen evolution had ceased, and dissolving the residue in dimethylformamide (1 ml). The reaction mixture was stirred at 0° for 4 hours and then poured into ethyl acetate and extracted several times with water. The organic phase was dried and evaporated to give the p-methoxybenzylmercapto derivative which was purified by preparative thin layer of chromatography (silica gel G, 20% ethyl acetate-benzene), 80 mg (72%).

A mixture of the above product (52 mg, 0.089 mmol), mercuric acetate (124 mg, 0.389 mmol), dichloromethane (0.4 ml) and methanol (1.3 ml) was stirred at room temperature under an argon atmosphere for 18 hours. Ether was added and the reaction mixture was filtered. The resulting solid was suspended in dichloromethane (5 ml) and cooled to 0°. Hydrogen sulfide was bubbled through the mixture for 40 minutes at 0° and then the solution was flushed with nitrogen. The suspension was filtered to remove the mercury sulfide and the filtrate was concentrated to give a residue which was chromatographed on preparative thin layer plates (silica gel G, 20% ethyl acetate-benzene) to give the title product.

EXAMPLE 14

When (cis-3-amino-2-bromomethyl-4-oxo-1-azetidinyl)-thioacetoxyacetic acid hydrochloride is acylated by standard acylation methods known in the art with the appropriate carboxylic acid or an activated derivative thereof in which any sensitive group(s) are appropriately protected, the following products are obtained after removal by standard methods of any protecting group(s):

[cis-3-phenylacetamido-2-bromomethyl-4-oxo-1-azetidinyl]thioacetoxyacetic acid

[cis-3-(α-hydroxyphenylacetamido)-2-bromomethyl-4-oxo-1-azetidinyl]thioacetoxyacetic acid

[cis-3-trifluoromethylmercaptoacetamido-2-bromomethyl-4-oxo-1-azetidinyl]thioacetoxyacetic acid

[cis-3-methylmercaptoacetamido-2-bromomethyl-4-oxo-1-azetidinyl]thioacetoxyacetic acid

[cis-3-methylsulfonylacetamido-2-bromomethyl-4-oxo-1-azetidinyl]thioacetoxyacetic acid

[cis-3-(2',2',2'-trifluoroethylsulfinylacetamido)-2-bromomethyl-4-oxo-1-azetindinyl]thioacetoxyacetic acid

[cis-3-cyanoacetamido-2-bromomethyl-4-oxo-1-azetidinyl]thioacetoxyacetic acid

[cis-3-cyanomethylmercaptoacetamido-2-bromomethyl-4-oxo-1-azetidinyl]thioacetoxyacetic acid

[cis-3-(α-carboxy-3'-thienylacetamido)-2-bromomethyl-4-oxo-1-azetidinyl]thioacetoxyacetic acid

[cis-3-(α-carboxyphenylacetamido)-2-bromomethyl-4-oxo-1-azetidinyl]thioacetoxyacetic acid

[cis-3-(1'-tetrazolylacetamido)-2-bromomethyl-4-oxo-1-azetidinyl]thioacetoxyacetic acid

[cis-3-(4'-pyridylmercaptoacetamido)-2-bromomethyl-4-oxoazetidinyl]thioacetoxyacetic acid

[cis-3-(syn-α-methoxyimino-2'-furylacetamido)-2-bromomethyl-4-oxo-1-azetidinyl]thioacetoxyacetic acid

[cis-3-(α-oximinophenylacetamido)-2-bromomethyl-4-oxo-1-azetidinyl]thioacetoxyacetic acid

EXAMPLE 15

When each product of Example 14, preferably as its sodium or potassium salt, is treated with cyclohexylamine by the procedure set forth in Example 9 the following products are obtained as their cyclohexylamine salts:

6β-phenylacetamido-7-oxo-3-thia-1-azabicyclo-[3.2.0]heptane-2-carboxylic acid
6β-(α-hydroxyphenylacetamido)-7-oxo-3-thia-1-azabicyclo[3.2.0]heptane-2-carboxylic acid
6β-trifluoromethylmercaptoacetamido-7-oxo-3-thia-1-azabicyclo[3.2.0]heptane-2-carboxylic acid
6β-methylmercaptoacetamido-7-oxo-3-thia-1-azabicyclo[3.2.0]heptane-2-carboxylic acid
6β-methylsulfonylacetamido-7-oxo-3-thia-1-azabicyclo[3.2.0]heptane-2-carboxylic acid
6β-(2',2',2'-trifluoroethylsulfinylacetamido)-7-oxo-3-thia-1-azabicyclo[3.2.0]heptane-2-carboxylic acid
6β-cyanoacetamido-7-oxo-3-thia-1-azabicyclo-[3.2.0]heptane-2-carboxylic acid
6β-cyanomethylmercaptoacetamido-7-oxo-3-thia-1-azabicyclo[3.2.0]heptane-2-carboxylic acid
6β-(α-carboxy-3'-thienylacetamido)-7-oxo-3-thia-1-azabicyclo[3.2.0]heptane-2-carboxylic acid
6β-(α-carboxyphenylacetamido)-7-oxo-3-thia-1-azabicyclo[3.2.0]heptane-2-carboxylic acid
6β-(1'-tetrazolylacetamido)-7-oxo-3-thia-1-azabicyclo[3.2.0]heptane-2-carboxylic acid
6β-(4'-pyridylmercaptoacetamido)-7-oxo-3-thia-1-azabicyclo[3.2.0]heptane-2-carboxylic acid
6β-(syn-α-methoxyimino-2'-furylacetamido)-7-oxo-3-thia-1-azabicyclo[3.2.0]heptane-2-carboxylic acid
6β-(α-oximinophenylacetamido)-7-oxo-3-thia-1-azabicyclo[3.2.0]heptane-2-carboxylic acid.

EXAMPLE 16

6β-azido-7-oxo-3-thia-1-azabicyclo[3.2.0]heptane-2-carboxylic acid

The ester from Example 1 (20 mg, 0.066 mmol) was dissolved in tetrahydrofuran (5 ml) and water (5 ml). The solution under argon was treated with 1 ml of a basic solution of pH 9.2 (3.3 g $K_2CO_3$ and 2 g of $NaHCO_3$ in 40 ml water). The reaction mixture was stirred for 55 minutes at room temperature and the organic solvent was removed. The basic aqueous phase was washed with ethyl acetate, adjusted to pH 2 with phosphoric acid and extracted with ethyl acetate. The extracts were washed with brine, dried and evaporated to give the title product, 11.7 mg (83%).

We claim:
1. A compound of the formula

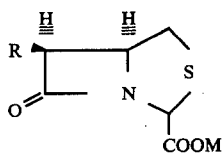

wherein
R is acylamino, azido, or amino;
acyl is a pharmaceutically acceptable acyl group known to be useful to impart antibacterial activity when used as a substituent on the 7 or 6 position amino group of cephalosporins or penicillins; and
M is hydrogen, a pharmaceutically acceptable cation or a removable carboxylic acid protecting ester.

2. A compound as claimed in claim 1 where R is acylamino.

3. A compound as claimed in claim 2 where acyl is X—CHCO, Y—CH$_2$CO, or Z—S(O)$_n$CH$_2$CO;
      |
      A X is thienyl, furyl, cyclohexyl, cyclohexenyl, cyclohexadienyl, phenyl or phenyl substituted with one or two substituents selected from the group consisting of lower alkyl, lower alkoxy, hydroxy, hydroxymethyl, halo, nitro, mercapto, lower alkylthio, trifluoromethyl, ureido, formamido, and carboxymethylamino;
A is hydroxy, formyloxy, carboxy, sulfo or (when the α-hydrogen is absent) methoxyimino or oximino;
Y is cyano, azido, phenyl, phenoxy, or a heterocyclic ring selected from the group consisting of thienyl, furyl, thiazolyl, isothiazolyl, oxadiazolyl, thiadiazolyl, triazolyl, tetrazolyl, pyridyl, and pyrimidyl, each heterocyclic ring being unsubstituted or substituted with one or two substituents selected from the group consisting of lower alkyl, halo, hydroxy, nitro, lower alkoxy, phenyl and phenylalkyl;
Z is phenyl, pyridyl, lower alkyl, trifluoromethyl, trifluoromethyl, or cyanomethyl;
n is 0, 1 or 2; and
M is hydrogen or a pharmaceutically acceptable cation.

4. A compound as claimed in claim 3 where acyl is mandeloyl, α-formyloxyphenylacetyl, trifluoromethylmercaptoacetyl, methylmercaptoacetyl, methylsulfonylacetyl, 2,2,2-trifluoroethylsulfinylacetyl, cyanoacetyl, cyanomethylmercaptoacetyl, α-carboxy-2-thienylacetyl, α-carboxy-3-thienylacetyl, α-carboxyphenylacetyl, α-sulfophenylacetyl, 2-thienylacetyl, 1-tetrazolylacetyl, phenoxyacetyl, phenylacetyl, 4-pyridylmercaptoacetyl, α-syn-methoxyimino(2-furyl)acetyl, or α-oximinophenylacetyl.

5. A compound as claimed in claim 4 being the compound 6β-phenoxyacetamido-7-oxo-3-thia-1-azabicyclo[3.2.0]-heptane-2-carboxylic acid and its cyclohexylamine, sodium or potassium salt.

6. A compound as claimed in claim 4 being the compound 6β-(2-thienylacetamido)-7-oxo-3-thia-1-azabicyclo-[3.2.0]heptane-2-carboxylic acid and its cyclohexylamine, sodium or potassium salt.

7. A compound as claimed in claim 1 where R is amino and M is a removable carboxylic acid protecting ester.

8. A compound as claimed in claim 7 where R is amino and M is methyl, benzyl or benzhydryl.

9. A compound as claimed in claim 8 being the compound benzyl 6β-amino-7-oxo-3-thia-1-azabicyclo[3.2.0]heptane-2-carboxylate.

10. A compound as claimed in claim 8 being the compound benzhydryl 6β-amino-7-oxo-3-thia-1-azabicyclo-[3.2.0]heptane-2-carboxylate.

11. A compound as claimed in claim 1 where R is azido and M is hydrogen or a removable carboxylic acid protecting ester.

12. A compound as claimed in claim 11 being the compound 6β-azido-7-oxo-3-thia-1-azabicyclo[3.2.0-]heptane-2-carboxylic acid.

13. A compound as claimed in claim 12 being the benzhydryl ester.

14. A compound as claimed in claim 12 being the benzyl ester.

15. A process for preparing compounds of claim 1 where R is acylamino or azido comprising treating a compound of the formula

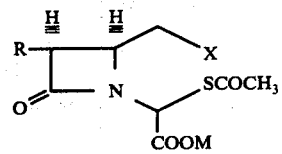

where
R is acylamino or azido;
  acyl is a pharmaceutically acceptable acyl group known to be useful to impart antibacterial activity when used as a substituent on the 7 or 6 position amino group of cephalosporins or penicillins;
X is halogen and
M is hydrogen, alkali metal cation or a removable carboxylic acid protecting group, with a cyclohexylamine.

* * * * *

UNITED STATES PATENT AND TRADEMARK OFFICE
CERTIFICATE OF CORRECTION

PATENT NO. : 4,122,086
DATED : October 24, 1978
INVENTOR(S) : Ralph Floyd Hall and William Francis Huffman It is certified that error appears in the above-identified patent and that said Letters Patent are hereby corrected as shown below:

Column 18, line 30, change --trifluoromethyl-- to "trifluoroethyl"

Column 18, line 35, change --mandeloly-- to "mandeloyl"

Signed and Sealed this

Twenty-seventh Day of March 1979

[SEAL]

Attest:

RUTH C. MASON
Attesting Officer

DONALD W. BANNER
Commissioner of Patents and Trademarks